United States Patent
Babic

(10) Patent No.: US 11,492,394 B1
(45) Date of Patent: Nov. 8, 2022

(54) KITS AND CONTAINERS FOR TREATING VIMENTIN EXPRESSING TUMORS

(71) Applicant: Nascent Biotech, Inc., Vero Beach, FL (US)

(72) Inventor: Ivan Babic, San Diego, CA (US)

(73) Assignee: Nascent Biotech, Inc., Vero Beach, FL (US)

( * ) Notice: Subject to any disclaimer, the term of this patent is extended or adjusted under 35 U.S.C. 154(b) by 0 days.

(21) Appl. No.: 17/515,010

(22) Filed: Oct. 29, 2021

(51) Int. Cl.
*C07K 16/18* (2006.01)
*A61K 47/68* (2017.01)
*A61J 1/14* (2006.01)
*A61P 35/00* (2006.01)

(52) U.S. Cl.
CPC ............ *C07K 16/18* (2013.01); *A61J 1/1468* (2015.05); *A61K 47/6843* (2017.08); *A61P 35/00* (2018.01); *C07K 2317/51* (2013.01)

(58) Field of Classification Search
None
See application file for complete search history.

(56) References Cited

U.S. PATENT DOCUMENTS

| | | | |
|---|---|---|---|
| 8,815,247 B2 | 8/2014 | Govindappa et al. | |
| 11,028,155 B2 | 6/2021 | Glassy et al. | |
| 2002/0009444 A1 | 1/2002 | Grillo-Lopez | |
| 2002/0099179 A1 | 7/2002 | Jolliffe et al. | |
| 2011/0256135 A1* | 10/2011 | Fraunhofer | A61K 39/39591 424/135.1 |
| 2013/0287802 A1 | 10/2013 | Govindappa et al. | |
| 2015/0218280 A1 | 8/2015 | Epstein et al. | |
| 2017/0073400 A1* | 3/2017 | Glassy | A61K 47/6865 |
| 2018/0243415 A1 | 8/2018 | Mallik et al. | |

FOREIGN PATENT DOCUMENTS

| | | |
|---|---|---|
| WO | 1989001343 A1 | 2/1989 |
| WO | 2013055404 A1 | 4/2013 |
| WO | 2014072741 A1 | 5/2014 |
| WO | 2017044866 A2 | 3/2017 |
| WO | 2017044866 A3 | 6/2017 |

OTHER PUBLICATIONS

"Nascent Biotech's Pritumumab: The Future of Brain Cancer Immunotherapy", Available Online at: https://born2invest.com/articles/nascent-biotechs-pritumumab-the-future-of-brain-cancer-immunotherapy, Mar. 31, 2015, 14 pages.

Boado et al., "Humanization of Anti-Human Insulin Receptor Antibody for Drug Targeting Across the HumanBlood-Brain Barrier", Biotechnology and Bioengineering, vol. 96, No. 2, 2007, pp. 381-391.

Chen et al., "Monoclonal Antibody Therapy for Malignant Glioma", Advances in Experimental Medicine and Biology, vol. 746, 2012, pp. 121-141.

Glassy et al., "Summary Analysis of the Pre-Clinical and Clinical Results of Brain Tumor Patients Treated With Pritumumab", Human Antibodies, vol. 18, Issue 4, 2009, pp. 127-137.

Kubo et al., "Monoclonal Immunotherapy With Human Monoclonal Antibody ( Cln-igg) In Glioma Patients", Nippon Rinsho, vol. 60, No. 3, 2002, pp. 497-503.

Vincke et al., "General Strategy to Humanize a Camelid Single-Domain Antibody and Identification of a Universal Humanized Nanobody Scaffold", Journal of Biological Chemistry, vol. 284, No. 5, Jan. 30, 2009, pp. 3273-3284.

Williams et al., "Humanising Antibodies by CDR Grafting", Antibody Engineering, vol. 1, 2010, pp. 319-339.

Glassy et al., "Summary Analysis of the Pre-Clinical and Clinical Results of Brain Tumor Patients Treated with Pritumumab", Hum Antibodies, vol. 18, No. 4, Jan. 2009, pp. 127-137.

Gupta et al., "Human Hybridoma and Recombinant Pritumumab Antibodies for Treatment of Human Solid Tumors", Journal for ImmunoTherapy of Cancer, vol. 2, No. S3, Nov. 6, 2014, p. 149.

PCT/US2021/057313 , International Search Report and Written Opinion, dated Jan. 26, 2022, 11 pages.

Steinmetz et al., "Two Domains of Vimentin are Expressed on the Surface of Lymph Node, Bone and Brain Metastatic Prostate Cancer Lines along with the Putative Stem Cell Marker Proteins CD44 and CD133", Cancers, vol. 3, No. 3, Jul. 2011, pp. 2870-2885.

Tica et al., "Combined Transcriptomics, Proteomics and Bioinformatics Identify Drug Targets in Spinal Cord Injury", International Journal of Molecular Sciences, vol. 19, No. 5, May 14, 2018, pp. 1-19.

\* cited by examiner

*Primary Examiner* — Nelson B Moseley, II
(74) *Attorney, Agent, or Firm* — Kilpatrick Townsend & Stockton LLP

(57) ABSTRACT

Provided herein are containers comprising a composition comprising an antibody comprising a heavy chain comprising SEQ ID NO:1 and a light chain comprising SEQ ID NO:2. The containers can be bottles or vials, for example, glass or polyethylene terephthalate G (PETG) bottles or vials. Also provided are kits comprising the containers and methods of treating cancer using the antibodies from the containers.

20 Claims, 7 Drawing Sheets

Specification includes a Sequence Listing.

SEQUENCE LISTING

<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Synthetic Construct

<400> SEQUENCE: 1

-continued

```
Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Pro Ser Gly Gly Ser Thr Asn Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Val Glu Asp Thr Ala Val Tyr Ile Cys
                85                  90                  95

Gly Arg Val Pro Tyr Arg Ser Thr Trp Tyr Pro Leu Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu His Ser Lys Val Pro Thr Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Thr Tyr Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

US 11,492,394 B1

KITS AND CONTAINERS FOR TREATING VIMENTIN EXPRESSING TUMORS

REFERENCE TO A "SEQUENCE LISTING" SUBMITTED AS ASCII TEXT FILE VIA EFS WEB

The instant application contains a Sequence Listing which has been submitted electronically in ASCII format and is hereby incorporated by reference in its entirety. Said ASCII copy, created on Oct. 29, 2021, is named Sequence_Listing_US_ST25.txt and is 6,106 bytes in size.

BACKGROUND

The blood brain barrier (BBB) poses a significant barrier for the delivery of therapeutics to the brain. The BBB is a protective endothelial tissue surrounding the CNS and poses a major obstacle to the systemic delivery of therapeutic and diagnostic agents for the treatment of neurological diseases. For example, treatment of brain cancer or metastases of other solid tumors to the brain is a highly unmet need. The lack of good treatments is due to the invasive and infiltrating character of tumors in the brain, and the inability of most effective biologic agents to cross the BBB. If the BBB were leaky or can readily be overcome, then new and useful drugs could be delivered to brain tissues. Previous products designed to overcome or bypass the BBB have been difficult to control thereby limiting their usefulness. The present disclosure satisfies these and other needs by providing antibodies or antibody fragments that are able to cross the BBB.

SUMMARY

Provided herein are containers comprising a composition comprising an antibody comprising a heavy chain comprising SEQ ID NO:1 and a light chain comprising SEQ ID NO:2. The containers can be bottles or vials, for example, glass or polyethylene terephthalate G (PETG) bottles or vials. Also provided are kits comprising the containers and methods of treating cancer using the antibodies from the containers.

DETAILED DESCRIPTION

Figure 1:
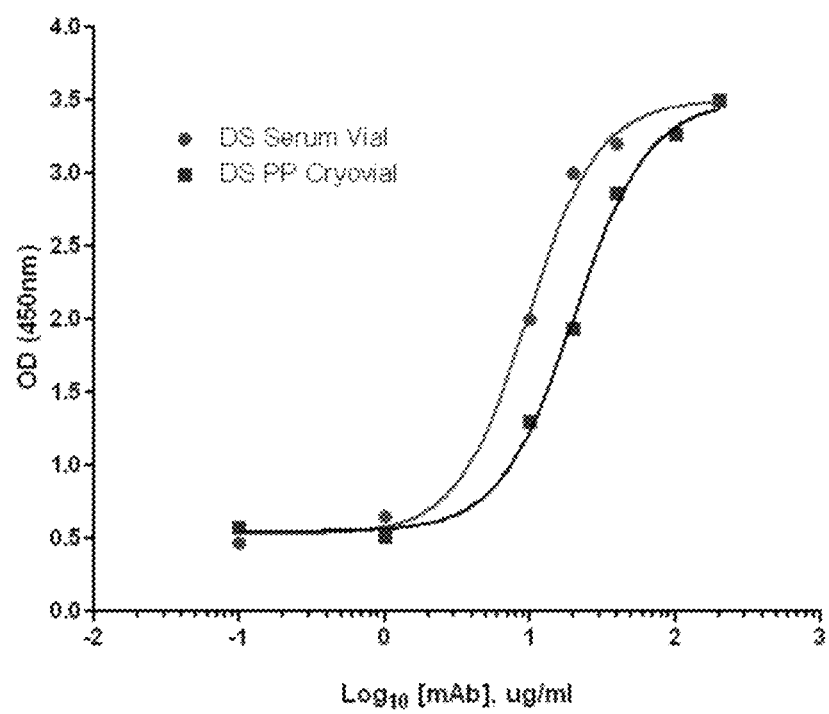
FIG. 1 is a graph showing clinical drug substance antibody lots stored in PETG serum vials is more potent than clinical drug substance antibody lots stored in polypropylene (PP) vials.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

"Vertebrate," "mammal," "subject," "mammalian subject," or "patient" are used interchangeably and refer to mammals such as human patients and non-human primates, as well as experimental animals such as rabbits, rats, and mice, cows, horses, goats, and other animals. Animals include all vertebrates, e.g., mammals and non-mammals, such as mice, sheep, dogs, cows, avian species, ducks, geese, pigs, chickens, amphibians, and reptiles.

"Treating" or "treatment" refers generally to either (i) the prevention of disease, e.g., prophylaxis, or (ii) the reduction or elimination of symptoms of a disease of interest, e.g., therapy. Thus, treatment can be prophylactic (to prevent or delay the onset of the disease, or to prevent the manifestation of clinical or subclinical symptoms thereof) or therapeutic suppression or alleviation of symptoms after the manifestation of the disease.

"Preventing" or "prevention" refers to prophylactic administration with compositions of the invention.

"Therapeutically-effective amount" or "an effective amount" refers to an amount of an antibody composition that is sufficient to prevent a disease or to alleviate (e.g., mitigate, decrease, reduce) at least one of the symptoms associated with a disease. It is not necessary that the administration of the composition totally eliminate the symptoms of the disease, as long as the benefits of administration of the composition outweigh the detriments. Likewise, the terms "treat" and "treating" in reference to a disease, as used herein, are not intended to mean that the subject is necessarily cured of the disease or that all clinical signs thereof are eliminated, only that some alleviation or improvement in the condition of the subject is effected by administration of the composition.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, glioblastoma, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

As used herein, the term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term, including IgA, IgD, IgE, IgG, and IgM.

An intact "antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature, 341:544-546 (1989)), which consists of a $V_H$ domain; and (vi) an isolated complementarity determining region (CDR).

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242).

As used herein, the term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments and can be prepared by recombinant techniques or enzymatic or chemical cleavage of intact antibodies.

Provided herein are containers comprising an antibody comprising a heavy chain comprising SEQ ID NO:1 and a light chain comprising SEQ ID NO:2. Optionally, the containers comprise a pharmaceutical composition comprising the antibody. Optionally, the containers comprise a therapeutically effective amount of the antibody. Optionally, the container is a bottle or vial. Optionally, the containers can be made out of glass or polyethylene terephthalate G (PETG). Optionally, the container is a glass vial or a PETG vial. Optionally, the container is a vial and the vial comprises from 5 mg/ml to 15 mg/ml of the antibody.

These sequences of the provided antibody are shown below:

```
                                              SEQ ID NO. 1:
EVQLLESGGDLVQPGGSLRLSCAASGFTFSNYAMSWVRQAPGKGLEWVS

AITPSGGSTNYADSVKGRFTISRDNSQNTLYLQMNSLRVEDTAVYICGR

VPYRSTWYPLYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

EPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

SEQ ID NO:2:
DIQMTQSPSSLSASVGDRVTITCRASQDISNYLAWFQQKPGKAPKSLIY

AASSLHSKVPTQFSGSGSGTDFTLTISSLQPEDFATYYCLQYSTYPITF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Optionally, the antibody has an isoelectric point of 8.0-9.0. Optionally, the antibody has an isoelectric point of about 8.7.

Optionally, e.g., bottle or vial, the antibody has a median binding effective concentration (EC50) of between 8 to 9 ug/ml. Optionally, in the glass container, the EC50 of the antibody in the glass vial is between 8 to 9 ug/ml. Optionally, in the PETG container, the EC50 of the antibody in the glass vial is between 9 to 12 ug/ml. Optionally, the EC50 values of the antibody are those as determined using the conditions described in the examples. In other words, the antibody can have an EC50 value between 9 to 12 ug/ml under the conditions described in the examples below.

The herein provided antibody comprising a heavy chain comprising SEQ ID NO:1 and a light chain comprising SEQ ID NO:2, sometimes referred to as pritumumab, crosses the blood brain barrier. See, for U.S. Pat. No. 11,028,155, which is incorporated by reference herein in its entirety. In addition, as described in the examples, the antibody binds vimentin. Optionally, the vimentin is located on the surface of a cancer cell or has been secreted by the cancer cell and is located externally to the cancer cell. Optionally, the cancer is brain cancer.

The containers containing the antibodies can be stored over a long period of time. Optionally, the period of time is 3, 6, 9, 12, 15, 18, 21, or 24 months or longer. Optionally, the antibodies can be stored at a temperature of −60° C. or below. Optionally, the antibody retains its activity over 3 freeze/thaw cycles.

As described below, the antibody can be conjugated to an agent. Optionally, the agent is a therapeutic agent or a diagnostic agent. Optionally, the therapeutic agent is a chemotherapeutic agent. Optionally, the diagnostic agent is a fluorescent agent, radioactive agent or chemiluminescent agent.

Also provided are methods of delivering an antibody across a blood brain barrier comprising administering the herein provided antibody from the containers, e.g., bottles or vials, described herein to a subject thereby delivering the antibody across the blood brain barrier. Optionally, the containers are glass or PETG containers.

As described above, the provided antibodies disclosed herein can be conjugated to an agent, e.g., a therapeutic moiety, such as a cytotoxin, a drug (e.g., an immunosuppressant) or a radiotoxin. Such conjugates are referred to herein as "immunoconjugates".

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Since pritumumab can cross the blood brain barrier it can be used as a delivery vehicle for delivering other agents, e.g., imaging or therapeutic agents to the brain or other tumor tissues. Thus, provided are composition comprising an antibody comprising a heavy chain and a light chain, the heavy chain comprising a sequence of SEQ ID NO:1 and the light chain comprising a sequence of SEQ ID NO:2 and one or more agents, e.g., imaging or therapeutic agents. Optionally, the agents are conjugated to the antibody. Optionally, the therapeutic agent is a chemotherapeutic agent. Optionally, the conjugate comprises a recombinant antigen binding protein as described herein conjugated to one or more agents. Optionally, the composition is formulated for delivery to the brain. Optionally, the composition is capable of crossing the blood brain barrier. Optionally, the heavy chain of the antibody comprises SEQ ID NO:1 and the light chain comprises SEQ ID NO:2. Optionally, the antibody is pritumumab.

Techniques for conjugating such therapeutic moieties to antibodies are well known, see, e.g., Amon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates," Immunol. Rev., 62:119-58 (1982).

Suitable therapeutic agents for use in the provided compositions and methods, e.g., for conjugation to the provided antibodies include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

As described herein, the antibodies can be linked or conjugated to an imaging agent. Imaging agents and their use are known. Optionally, the imaging agent is a "detectable moiety," which is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego. The detectable moiety can be selected from the group consisting of gamma-emitters, beta-emitters, and alpha-emitters, gamma-emitters, positron-emitters, X-ray-emitters and fluorescence-emitters. Suitable fluorescent compounds include fluorescein sodium, fluorescein isothiocyanate, phycoerythrin, and Texas Red sulfonyl chloride, Allophycocyanin (APC), Cy5-PE, CY7-APC, and Cascade yellow.

Optionally the detectable moiety can be visualized using histochemical techniques, ELISA-like assays, confocal microscopy, fluorescent detection, cell sorting methods, nuclear magnetic resonance, radioimmunoscintigraphy, X-radiography, positron emission tomography, computerized axial tomography, magnetic resonance imaging, and ultrasonography.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

The presently disclosed subject matter provides containers comprising pharmaceutical compositions comprising the antibodies provided in the present disclosure. Optionally, the antibodies according to the present disclosure can be administered to subjects with one or more additional agents, for example, antiviral or anticancer drugs or analgesics.

Pharmaceutical compositions can also contain a pharmaceutically acceptable carrier or adjuvant for administration of the antibody or antigen binding protein. Optionally, the carrier is pharmaceutically acceptable for use in humans. The carrier or adjuvant should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, ammo acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated as tablets, pills, dragees, capsules, liquids, gels, syrups, slurries and suspensions, for ingestion by the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) Cancer Res 54:5408-5413; Saltzman & Fung (1997) Adv Drug Deliv Rev 26:209-230), a glycosaminoglycan (U.S. Pat. No. 6,106,866), a fatty acid (U.S. Pat. No. 5,994,392), a fatty emulsion (U.S. Pat. No. 5,651, 991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490, 840, and 5,855,900), and a polysome (U.S. Pat. No. 5,922, 545).

Antibody sequences can be coupled to active agents or carriers using methods known in the art, including but not limited to carbodiimide conjugation, esterification, sodium periodate oxidation followed by reductive alkylation, and glutaraldehyde crosslinking (Goldman et al. (1997) Cancer Res. 57:1447-1451; Cheng (1996) Hum. Gene Ther. 7:275-282; Neri et al. (1997) Nat. Biotechnol. 15:1271-1275; Nabel (1997) Vectors for Gene Therapy. In Current Protocols in Human Genetics, John Wiley & Sons, New York; Park et al. (1997) Adv. Pharmacol. 40:399-435; Pasqualini et al. (1997) Nat. Biotechnol. 15:542-546; Bauminger & Wilchek (1980) Meth. Enzymol. 70:151-159; U.S. Pat. No. 6,071,890; and European Patent No. 0 439 095).

A therapeutic composition of the present invention comprises in some embodiments a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the present disclosure can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Pharmaceutical compositions can include an effective amount of one or more antibodies as described herein. In some embodiments, a pharmaceutical composition can comprise an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and therapeutics or combination of therapeutics selected for administration. The effective amount for a given situation is determined by routine experimentation as practiced by one of ordinary skill in the art.

The pharmaceutical compositions of the invention can be administered in a variety of unit dosage forms depending upon the method of administration. Dosages for typical antibody pharmaceutical compositions are well known to those of skill in the art. Such dosages are typically advisory in nature and are adjusted depending on the particular therapeutic context or patient tolerance. The amount antibody adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

Also provided herein, are methods of treating vimentin-expressing cancer in a subject comprising administering the antibody from the herein provided containers, e.g., bottles or vials, to the subject thereby treating the vimentin-expressing cancer in the subject. Optionally, the containers are glass or PETG containers. Optionally, brain cancer and pancreatic cancer. Optionally, the brain cancer is a glioblastoma. Optionally, the subject is administered a therapeutically effective amount of the composition.

For purposes of the present invention, a therapeutically effective amount of a composition comprising an antibody, contains about 0.05 to 1500 µg protein, preferably about 10 to 1000 µg protein, more preferably about 30 to 500 µg and most preferably about 40 to 300 pg, or any integer between these values. For example, antibodies of the invention can be administered to a subject at a dose of about 0.1 µg to about 200 mg, e.g., from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg, with optional boosters given at, for example, 1 week, 2 weeks, 3 weeks, 4 weeks, two months, three months, 6 months and/or a year later. It is understood that the specific dose level for any particular patient depends upon a variety of factors including the activity of the specific antibody employed, the age, body weight, general health, sex, diet, time of administration, route of administration, and rate of excretion, drug combination and the severity of the particular disease undergoing therapy.

Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Compositions can be administered in a single dose treatment or in multiple dose treatments on a schedule and over a time period appropriate to the age, weight and condition of the subject, the particular antibody formulation used, and the route of administration.

Also provided herein are kits comprising the containers comprising the antibodies and instructions for use. Optionally, the containers have a label. Suitable containers include, for example, bottles, vials, and test tubes. The containers are formed from glass or PETG. The container holds a composition which includes the herein provided antibodies that is effective for therapeutic applications. The label on the container indicates that the composition is used for a particular therapy or non-therapeutic application, and can also indicate directions for either in vivo or in vitro use.

The following examples of specific aspects for carrying out the present invention are offered for illustrative purposes only, and are not intended to limit the scope of the present invention in any way.

EXAMPLES

Example 1. Storage Containers and Conditions Affect Antibody Activity

To determine whether the commercial storage vial containing the antibody pritumumab affects potency of the antibody, binding assays were performed on three different antibody lots. The first drug substance (DS) antibody lot was contained in either (i) Wheaton (#223739) clear glass serum bottles with 20 mm crimp top finish (10 ml size) (low-alkali borosilicate molded glass) at a concentration of 10 mg/ml concentration (approximately 4.5 ml volume) or (ii) in clear PETG serum vial (#1-0456-81P; ThermoFisher Scientific) lined continuous thread closure (5 ml size) at a concentration of 10 mg/ml (approximately 4 ml volume). The second DS antibody lot was contained in Nalgene cryogenic vials (#5000-1020) (1.5 ml size polypropylene (PP) screwtop vial) at a concentration of 9.9 mg/ml concentration (1 ml volume). The third antibody lot and reference standard used for potency assay is 9.72 mg/ml concentration (4 ml volume) in PETG serum vial (#1-0456-81P; ThermoFisher Scientific) lined continuous thread closure (5 ml size; polyethylene terephthalate G (PETG)).

The potency of the second antibody lot stored in the PP cryovial was compared to the first antibody lot stored in the clear PETG serum vial. The results in FIG. 1 show significant difference in potency between the drug substance (DS) stored in PP cryovial versus PETG serum vial. The EC50 for the clinical DS from PETG vial was 9.6 ug/ml while the EC50 for the PP cryovial was 20 µg/ml. The potency for the clinical DS lot stored in PETG serum vial (9.6 ug/ml) is similar to the potency for the clinical DS lot contained in glass serum containers (8.25 ug/ml). This result suggests that the difference in EC50 values between clinical drug substance and clinical drug product is a result of storage in different containers. The clinical DS lot stored in PP cryovials shows weak potency and may not be representative of the drug product material potency stored in glass serum containers.

Figure 2:
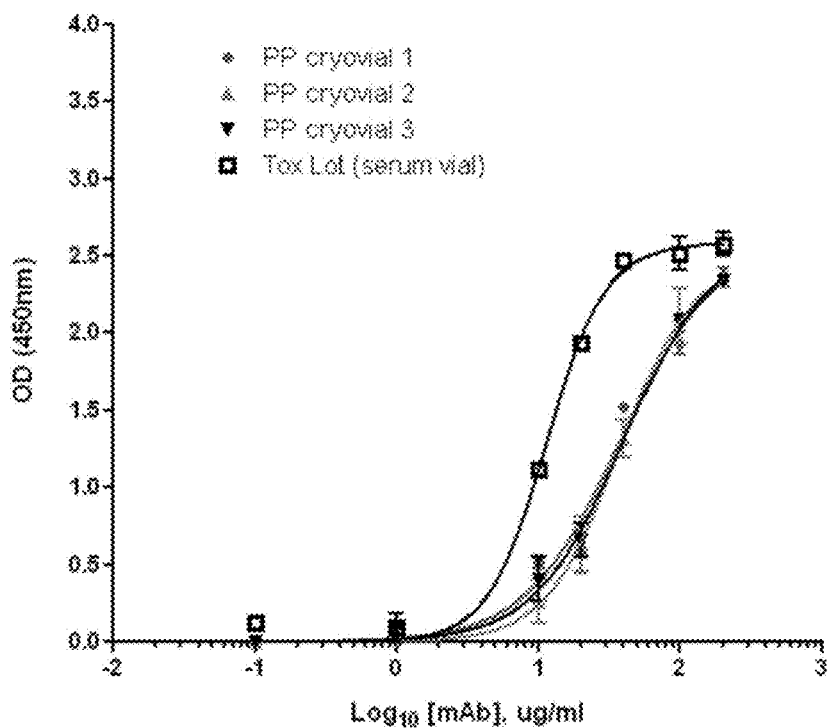
FIG. 2 is a graph showing the drug substance antibody lot used as a reference standard in toxicology assays has different potency in PP vials versus PETG vials. The antibody stored in PETG vials is more potent than antibody stored in PP vials.
Figure 3:
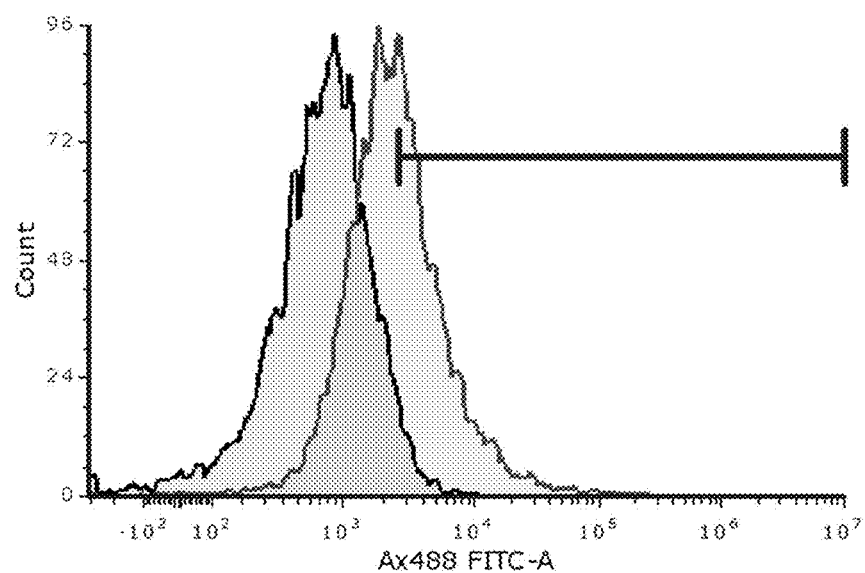
FIG. 3 is a histogram plot from flow cytometry showing pritumumab binds to the cell surface of U251 glioma cells. The left peak is unstained cells and the peak shifted to the right is pritumumab staining.
Figure 4:
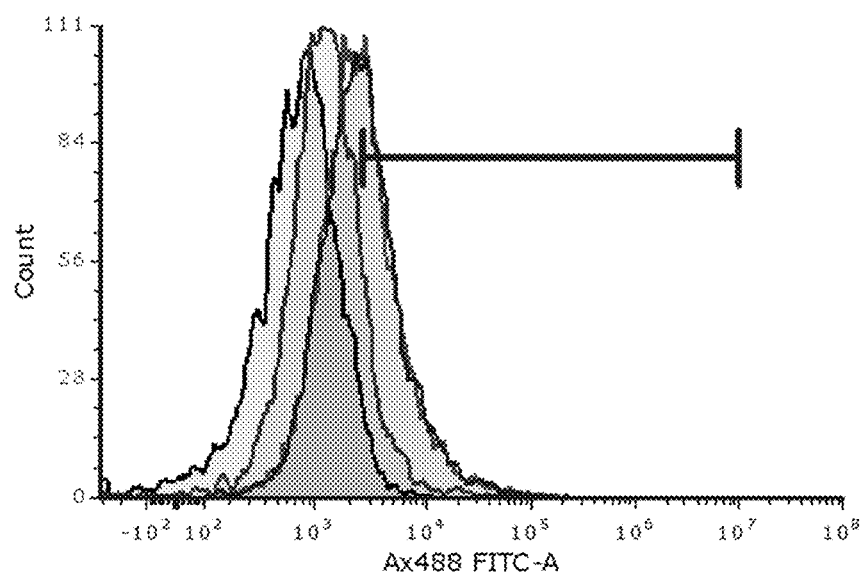
FIG. 4 is a graph showing recombinant human vimentin can compete pritumumab binding to glioma cells. The graph is a histogram plot showing unstained cells outlined in the far left peak, pritumumab alone (160 nM) outlined in the far right peak, pritumumab (160 nM)+vimentin (45 nM) is outlined in the far right peak overlapping the peak of pritumumab alone, and pritumumab (160 nM)+vimentin (450 nM) is outlined in the second peak from the left.

The potency of binding assay was performed to compare the third antibody DS lot and reference standard stored in PP cryovial and stored in PETG serum vial. ELISA binding assay was performed on 3 separate third antibody DS lots from PP cryovials with a third antibody DS lot from PETG serum vial. The results of FIG. 2 show that the DS lots stored in PP cryovials did not show the same potency as that stored in PETG serum vial. The PP cryovial stored DS lots had significantly lower binding (EC50 range 37 ug/ml to 40 µg/ml) compared to the DS lot from the PETG serum vial (EC50 of 11 ug/ml).

The binding ELISA assay compared clinical DS lots stored in PP cryovial with clinical DS lots stored in PETG serum vials. There was significant difference in potency between these samples. The EC50 value for the DS stored in PETG serum vial was similar to that reported for the clinical DS lot in glass containers and the Lot DS reference standard used for previous binding assays. Both the clinical DS stored in PP cryovials and the reference standard DS stored in PP cryovials is not representative of the drug product material (stored in glass serum vials) with respect to potency. However, both the clinical DS and toxicology DS stored in PETG serum vials shows EC50 values similar to the drug product material and is representative of the drug product with respect to potency.

In addition to the containers used to store antibodies, the storage conditions and formulations for the antibodies were tested. It was determined that product storage at 5° C. results in degradation of the antibody. Storage at temperature <−60° C. over 3 freeze-thaw cycles did not result in degradation. It is recommended/documented that this antibody be stored at temperatures below −60° C. for long-term storage. Further, the preferred concentration and formulation of the antibody in clinical product vials were determined to be approximately 10 mg/ml in 10 mM Sodium phosphate, 150 mM Sodium chloride pH7.0 (Phosphate-buffered saline (PBS)).

Example 2. Pritumumab Binds Specifically to Cell Surface of Glioma Cells and Shows Specificity for Vimentin To determine if pritumumab binds the surface of glioma cells, an assay was performed to determine if pritumumab can be competed away with recombinant human vimentin. The rationale of the experiment is to further demonstrate specificity of pritumumab antibody for extracellular vimentin.

FIGS. 1 and 2 show the results of flow cytometry experiments. Table 1 summarizes the binding competition experiment. Incubating 160 nM pritumumab with 45 nM recombinant vimentin does not outcompete U251 cells for binding. However, incubating 160 nM pritumumab with 2.5 molar excess recombinant vimentin (450 nM) can prevent pritumumab binding to the U251 cell surface.

TABLE 1

Percent of cells staining positive for Pritumumab.

|   |   | U251 % of gated cells |
|---|---|---|
|   | Unstained | 3.2 |
| 1 | Pritumumab alone (160 nM) | 42.5 |
| 2 | Pritumumab (160 nM) + vimentin (45 nM) | 44.2 |
| 3 | Pritumumab (160 nM) + vimentin (450 nM) | 12.4 |

The conclusion is recombinant vimentin is able to compete with pritumumab binding to the cell surface of glioma cells. This further demonstrates specificity of binding of pritumumab for vimentin.

To determine binding affinity of the antibody Pritumumab for vimentin. Octet HTX was employed to measure the antibody binding to human vimentin. Binding experiments were performed on Octet HTX at 25° C. Pritumumab (10 µg/ml) was loaded onto Anti-Human-Fc (AHC) biosensors. Loaded sensors were dipped into a serial of antigen dilutions (recombinant human vimentin) (300 nM start, 1:3 down, 7 points). Kinetic constants were calculated using a monovalent (1:1) model. The affinity of binding of the antibody, pritumumab, to vimentin was determined to be 7.55E-9M.

TABLE 2

Binding Kinetics of Pritumumab

| Sample ID | KD (M) | Kon (1/Ms) | Kdis (1/s) | Full X^2 | Full R^2 |
|---|---|---|---|---|---|
| Pritumumab | 7.55E-09 | 5.87E+04 | 4.43E-04 | 0.0156 | 0.9966 |

Example 3. Immunohistochemical Staining of CNS Tissue

The objective of this example was to determine if Pritumumab human monoclonal antibody stains central nervous system (CNS) neoplasms, particularly glioblastoma multifore and astrocytomas. These are the most common and aggressive primary CNS malignancies. To that end, immunohistochemical stains were performed on 80 human tissue cores. Seventy cores were from patients with glioblastomas and astrocytomas while 10 were from normal brains.

Glass slides containing unstained TMA cores of normal human and monkey subjects were obtained. From tissue blocks, paraffin section slides were cut and then dried overnight in a 60 degree oven. The slides were deparaffined with the heat-induced epitope retrieval technique using the Dako Target Retrieval Solution, ph 9.0 EDTA (Dako cat #S2367) in conjunction with pressure cooking for 30 minutes. The slides were then exposed to 3% $H_2O_2$ for 10 minutes in the DAKO Autostainer (model #S3800) and then exposed to the primary Pritumumab antibody diluted 1:10 for 2 hours at room temperature. Slides were then exposed to the Polymer-Horseradish Peroxidase anti-human lg/rabbit antibody for 30 minutes before exposing the slides to DAB for 10 minutes and counterstaining with hematoxylin for one minute prior to dehydrating them and adding the cover slip. The TMA cores were scanned using an Aperio ST Turbo scanner and links to the images made available for histo-morphologic examination and scoring. The viewing software is proprietary to HistoWiz.

Figure 5A:
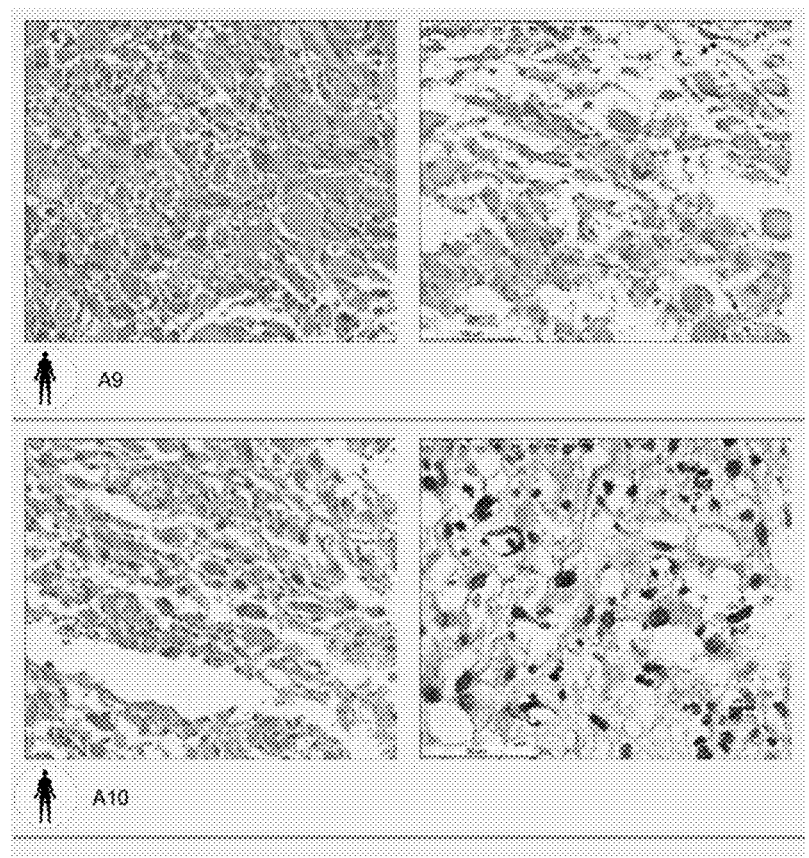
FIGS. 5A and 5B are photos of images from whole slide scans showing representative fields in central nervous system (CNS) neoplasms.
Figure 5B:
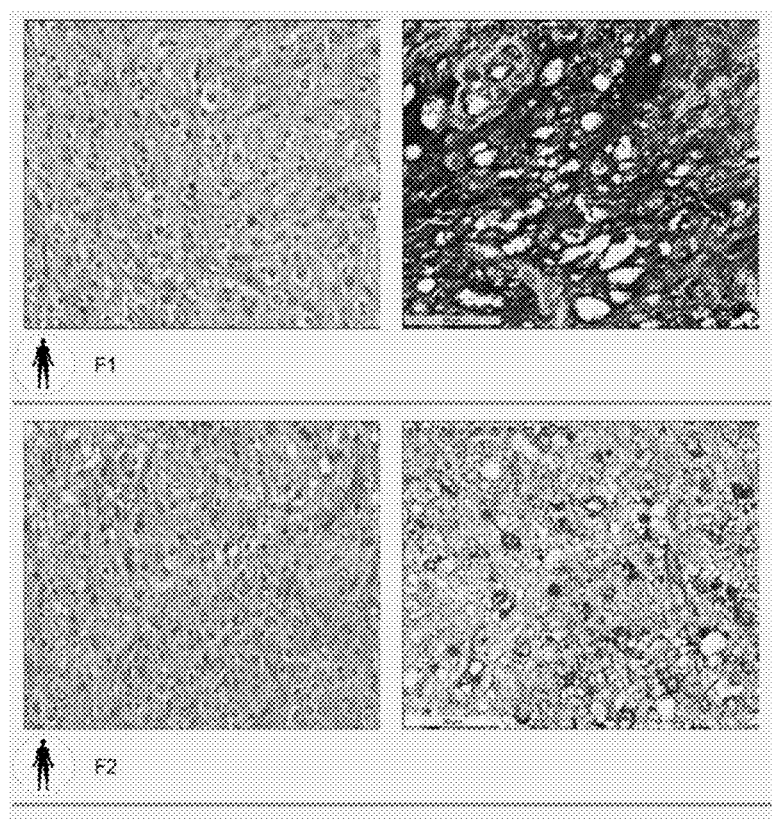
Figure 6A:
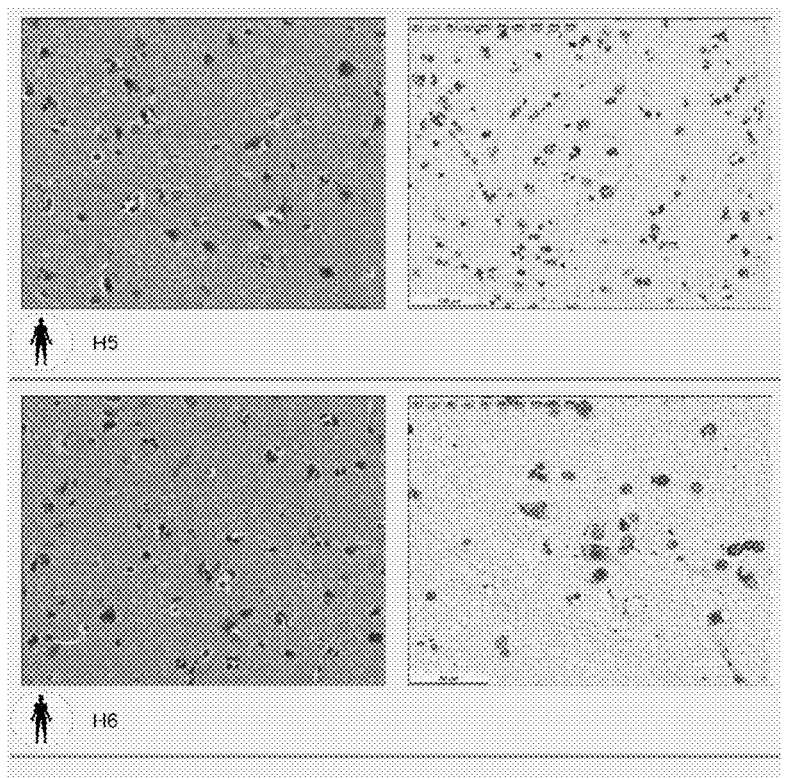
FIGS. 6A and 6B are photos of images from whole slide scans showing representative fields in normal cerebellum.
Figure 6B:
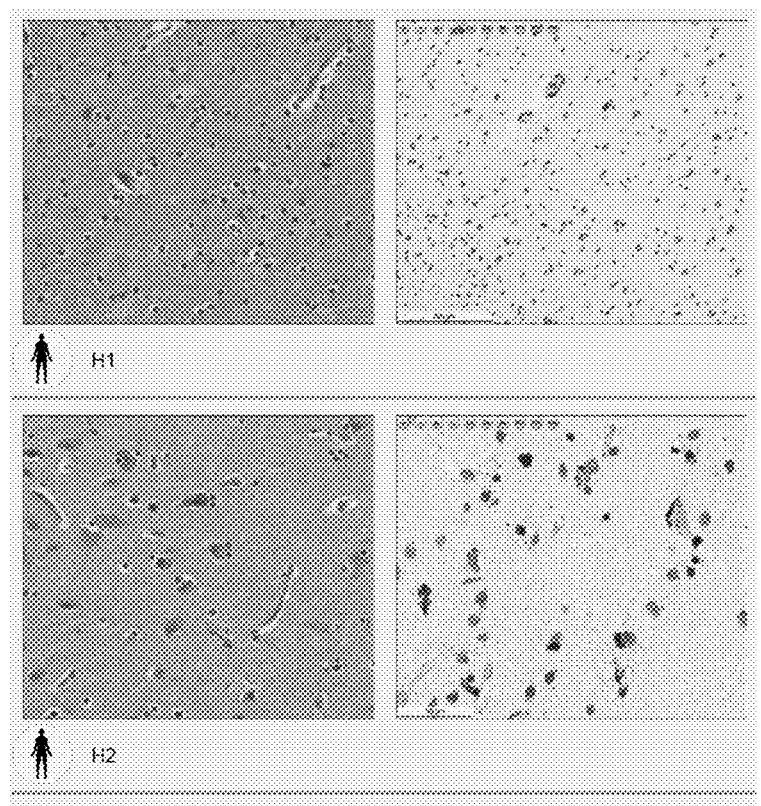

The TMA cores are from human brain (CNS) tissue, and consist of examples of glioblastoma, astrocytomas, and normal cerebrum. The human glioblastoma TMA cores all show either nuclear or cytoplasmic positivity. There is variability in staining intensity, but this was not a function of grade or type of glioblastoma. A rare case showed intense cytoplasmic staining (see FIGS. 5A and 5B). Glioblastomas with a gemistocytic pattern all showed moderate cytoplasmic staining. Low grade astrocytomas also demonstrated nuclear staining. Normal brain cores show staining of astroglial cells. Neurons demonstrate some granular cytoplasmic staining. See FIGS. 6A and 6B.

In summary, pritumumab demonstrated positivity in all of the astrocytomas and glioblastomas. There is variability of stain intensity from case to case. The predominate localization is nuclear. Cytoplasmic staining is usually weak or absent but one case demonstrated strong cytoplasmic staining.

What is claimed is:

1. A polyethylene terephthalate G (PETG) vial comprising an antibody comprising a heavy chain comprising SEQ ID NO:1 and a light chain comprising SEQ ID NO:2.

2. The vial of claim 1, wherein the antibody has an isoelectric point of 8.0-9.0.

3. The vial of claim 2, wherein the antibody has an isoelectric point of about 8.7.

4. The vial of claim 1, wherein the antibody is capable of crossing the blood brain barrier.

5. The vial of claim 1, wherein the antibody binds vimentin.

6. The vial of claim 5, wherein the vimentin is located on the surface of a cancer cell or secreted by a cancer cell.

7. The vial of claim 6, wherein the cancer is selected from the group consisting of brain cancer and pancreatic cancer.

8. The vial of claim 1, wherein the vial comprises from 5 mg/ml to 15 mg/ml of the antibody.

9. The vial of claim 1, wherein the antibody is conjugated to an agent.

10. The vial of claim 9, wherein the agent is a therapeutic agent or a diagnostic agent.

11. The vial of claim 10, wherein the therapeutic agent is a chemotherapeutic agent.

12. The vial of claim 10, wherein the diagnostic agent is a fluorescent agent, radioactive agent or chemiluminescent agent.

13. The vial of claim 1, wherein the vials can be stored over a long period of time.

14. The vial of claim 1, wherein the antibody retains its activity over 3 freeze/thaw cycles.

15. The vial of claim 1, wherein the antibody can be stored at a temperature of below −60° C.

16. A kit comprising the vial of claim 1 and instructions for use.

17. A method of delivering an antibody across a blood brain barrier comprising administering the antibody from the vial of claim 1 to a subject thereby delivering the antibody across the blood brain barrier.

18. A method of treating vimentin-expressing cancer in a subject comprising administering the antibody from the vial of claim 1, to the subject thereby treating the vimentin-expressing cancer in the subject.

19. The vial of claim 1, wherein the vial is stored for 3, 6, 9, 12, 15, 18, 21, or 24 months.

20. The vial of claim 1, wherein the antibody has increased potency compared to the antibody's activity in a polypropylene vial.

\* \* \* \* \*